US00PP25334P3

(12) United States Plant Patent
Marks

(10) Patent No.: US PP25,334 P3
(45) Date of Patent: Mar. 10, 2015

(54) ***HEMEROCALLIS* PLANT NAMED 'CONNIE MARKS'**

(50) Latin Name: ***Hemerocallis* sp.**
Varietal Denomination: Connie Marks

(76) Inventor: Randy Marks, Culpeper, VA (US)

( * ) Notice: Subject to any disclaimer, the term of this patent is extended or adjusted under 35 U.S.C. 154(b) by 163 days.

(21) Appl. No.: 13/507,872

(22) Filed: Aug. 3, 2012

(65) Prior Publication Data

US 2014/0041088 P1 Feb. 6, 2014

(51) Int. Cl.
*A01H 5/00* (2006.01)

(52) U.S. Cl.
USPC ..... Plt./312

(58) Field of Classification Search
CPC ..... A01H 5/02; A01H 5/0272
USPC ..... Plt./312
See application file for complete search history.

(56) References Cited

U.S. PATENT DOCUMENTS

PP10,975 P * 6/1999 Roberson ..... Plt./312

* cited by examiner

*Primary Examiner* — June Hwu
(74) *Attorney, Agent, or Firm* — Foley & Lardner LLP

(57) ABSTRACT

A new and distinct cultivar of *Hemerocallis* named 'Connie Marks' characterized by double, light yellow, fragrant flowers that are nocturnal, fully double, lightly creped and ruffled, 13.4 cm in diameter, and of considerable substance that blooms for 24 hours. 'Connie Marks' has a propensity to form a plurality of scapes per fan and two scapes per fan per bloom period; is heat and cold hardy to a wide range of Hardiness Zones-U.S.D.A. zones No. 3 to No. 7; has a delicate perfumed fragrance; and an extended bloom period from early June until the end of July which is longer than a thirty day or less average for more than 99% of cultivates currently in the trade. 'Connie Marks' cleanly sheds spent flowers to allow new buds to fully develop, readily propagates by division and exhibits a moderate rate of multiplication of three or more fans per year, and is resistant to daylily rust (*Puccinia hemerocallidis*.)

3 Drawing Sheets

Botanical classification: *Hemerocallis* sp.
Cultivar designation: 'Connie Marks'.

BACKGROUND OF THE DISCLOSURE

A new and distinct *Hemerocallis* cultivar 'Connie Marks', herein after also referred to as "the plant", is a new and distinct plant variety that has been asexually reproduced true to type by division in successive generations. It was discovered in a cultivated area when it first bloomed during the summer of 2001 at a commercial nursery/garden center located in Culpeper, Va. The plant 'Connie Marks' is the offspring of the daylily variety named 'Hyperion' which was registered in about 1925. 'Hyperion' was the only daylily growing in the nursery garden vicinity where 'Connie Marks' was discovered. The large 'Hyperion' clump had a smaller 6 fan, double yellow flowered 'Connie Marks' clump growing on its perimeter. 'Hyperion's' flowers are single. The plant has been successfully propagated by division methods at the same nursery to produce identical plants that maintain the unique characteristics of the original. Since 2001 the original 6 fan 'Connie Marks' has been repeatedly divided to produce numerous plants that are phenotypically identical.

*Hemerocallis hybrida* 'Hyperion' is the vegetative parent of 'Connie Marks', which is a mutation. There were no daylilies, except 'Hyperion,' growing in the larger nursery garden and due to physical structures of the nursery and surrounding 8 foot high arborvitae hedge, with no daylilies outside of the hedge, normal prevailing winds would not indicate pollen was windborne from a distant site.

SUMMARY OF THE INVENTION

The following traits have been repeatedly observed and represent the characteristics of 'Connie Marks'. These attributes, in combination, distinguish 'Connie Marks' as a new and distinct cultivar:

(1) 'Connie Marks' is a nocturnal, fully double, lightly creped and ruffled, 13.4 cm in diameter, light yellow daylily of considerable substance that blooms for 24 hours;
(2) 'Connie Marks' has a propensity to form a plurality of scapes per fan, two scapes per fan per bloom period;
(3) 'Connie Marks' is heat and cold hardy to a wide range of Hardiness Zones-U.S.D.A. zones No. 3-No. 7;
(4) 'Connie Marks' has a delicate perfumed fragrance;
(5) 'Connie Marks' has an extended bloom period from early June until the end of July which is longer than a thirty day average bloom period for more than 99% of cultivars currently in the trade which have bloom periods of less than thirty days;
(6) 'Connie Marks' cleanly sheds spent flowers to allow new buds to fully develop;
(7) The plant readily propagates by division and exhibits moderate rate of multiplication of three or more fans per fan per year; and
(8) 'Connie Marks' is resistant to daylily rust — *Puccinia hemerocallidis*.

Plants of the cultivar 'Connie Marks' can be compared to the parent cultivar *Hemerocallis hybrida* 'Hyperion' (unpatented). Plants of the instant cultivar 'Connie Marks' and plants of the cultivar 'Hyperion' differ in the following characteristics:

1. Plants of 'Connie Marks' have double flowers whereas plants of 'Hyperion' have single flowers.
2. Plants of 'Connie Marks' have smaller flowers than plants of 'Hyperion'.
3. Plants of 'Connie Marks' have petaloids with anthers, whereas plants of 'Hyperion' have the more typical anthers attached to filaments.
4. Plants of 'Connie Marks' exhibit more creping on the inner tepals than plants of 'Hyperion'.

Presently, the most commercially similar cultivar to the claimed cultivar 'Connie Marks' is the parent cultivar 'Hyperion', to which a comparison is provided above.

BRIEF DESCRIPTION OF THE PHOTOGRAPHS

The accompanying photographs of the new variety 'Connie Marks' demonstrate the overall appearance of the plant, including several unique traits. The colors shown are as accurate as reasonably possible with color reproductions of this type. Ambient light spectrum, source and direction may cause the appearance of minor variation in colors but in general the dominant color is a light lemon yellow. Color values cited in the detailed botanical description more accurately describe the actual colors of 'Connie Marks'.

DETAILED BOTANICAL DESCRIPTION

Figure 1:
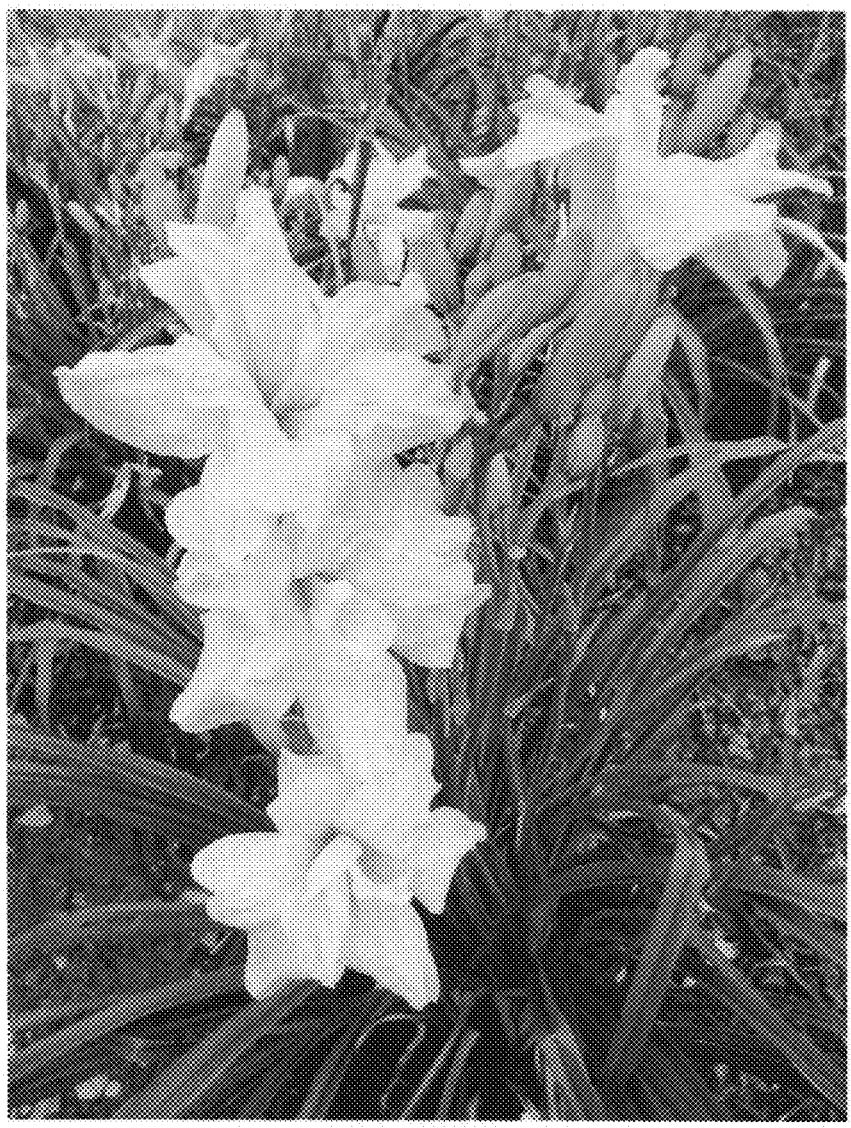
FIG. 1 shows a close-up frontal view of a typical plant of 'Connie Marks' with a clump of several flowers, buds, scapes, stems, etc. visible.
Figure 2:
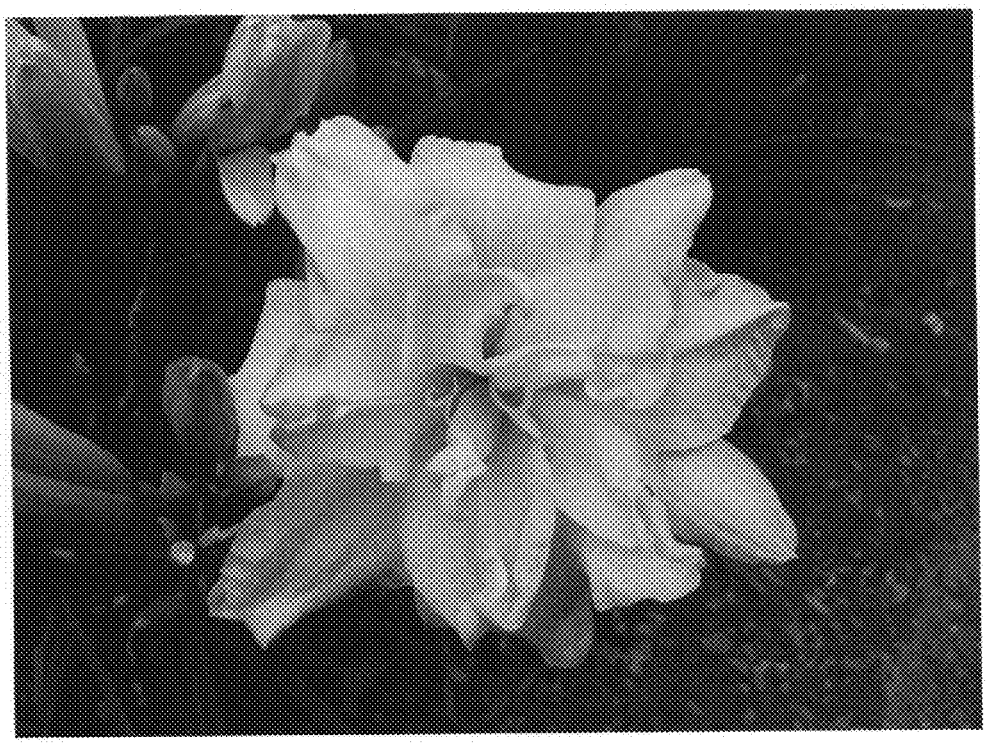
FIG. 2 shows a frontal view of a typical blossom of 'Connie Marks'.

The following is a detailed description of a three year old plant of the new cultivar as grown outdoors in a three gallon container in Culpeper, Va. The color determination is in accordance with The 2007 R.H.S. Colour Chart of The Royal Horticultural Society, London, England, except where general color terms of ordinary dictionary significance are used.

General characteristics:

*Bloom period*.—Early June until end of July.

*Plant habit*.—Herbaceous perennial, grass-like foliage.

*Height and spread*.—Hardy, deciduous, winter dormant, herbaceous rhizomatous perennial with basal linear leaves arching in upper ⅔s, natural foliage spread is generally 66 cm in diameter and generally 79 cm tall with an occasional leaf up to 90 cm tall and symmetrical.

*Hardiness*.—U.S.D.A. zones No. 3 to 7.

*Disease resistance*.—Has been observed to be resistant to daylily rust — *Puccinia hemerocallidis*.

*Root description*.—Fibrous roots.

*Propagation*.—Division; and.

*Growth rate*.—Moderate with three to four fans per fan season.

Foliage description:

*Leaf shape*.—Linear.

*Leaf division*.—Simple.

*Leaf base*.—Sheathed to crown.

*Leaf apex*.—Narrowly acute.

*Leaf venation*.—Longitudinal, parallel, same color as leaves.

*Leaf margin*.—Entire.

*Leaf attachment*.—Sheathed, not petioled.

*Leaf arrangement*.—Fan shaped.

*Leaf surface*.—Glabrous (without hairs).

*Leaf color*.—Mature leaves (upper and lower surface) R.H.S. Green Group upper leaf 137B and lower leaf 137C.

*Leaf size*.—Up to 90 cm in length, 0.5 to 2 cm wide; and.

*Leaf quantity*.—Approximately 150 leaves to 3 gallon pot.

Flower scape description:

*Scape shape*.—In approximately equal proportions scapes are ovoid, square, and round and ovoid at the base and all scapes are hollow.

*Scape number*.—Two per fan at one time.

*Scape aspect*.—Straight, held upright.

*Scape size*.—An average of 63.5 cm in length and 8 mm in width, branches average 3 cm in length and 4 mm in width.

*Scape color*.—R.H.S 138A, Green.

*Scape surface*.—Glabrous.

*Scape branching*.—Average three branches per scape, internode length 2 cm; and.

*Scape leaves*.—One per branch point plus two additional not at branch points, shortest at 1.2 cm long up to longest at 6.8 cm, not at branch, but on shaft, all leaves are glabrous. Color of scape leaves is not readily available.

Flower description:

*Inflorescence type*.—Scape bearing one to two double flowers simultaneously.

*Inflorescence size*.—An average of 6 cm deep and 13.4 cm in diameter.

*Flower duration*.—About twenty four hours, self cleaning.

*Flower number*.—Average of twelve per scape over entire blooming season.

*Flower aspect*.—Upward to outward.

*Flower bud color*.—Apex: R.H.S. 144C, Yellow-Green; longitudinally RHS 150B, Yellow-Green; longitudinal edges RHS 154A Yellow-Green.

*Flower bud shape*.—Oblanceolate, broadest width above the middle.

*Flower bud size*.—Average length 5.5 cm; average width 2 cm.

*Flower attachment*.—Pedunculate.

*Petal color*.—R.H.S. 7A, Yellow; on both sides, base has a light green throat, RHS 154B, Yellow-Green.

*Petal number*.—About 7 to 8 per flower.

*Petal shape*.—Broadly lanceolate with petaloid variety.

*Petaloid color*.—R.H.S. 7A, Yellow, with slight base, throat of RHS 154B, Yellow-Green.

*Petaloid number*.—About 4-5 per flower.

*Petaloid size*.—Average length about 70 mm; average width about 27.5 mm.

*Petaloid shape*.—Oblanceolate.

*Petal surface*.—Glabrous, waxy, mid-vein raised in upper surface, creped texture.

*Petal margins*.—Entire, and lightly ruffled, slightly irregular.

*Petal apex*.—Slightly irregular and rounded, obtuse.

*Petal size*.—Average width 4.3 cm and 10 cm long.

*Petal aspect*.—Slightly recurved.

*Sepal number*.—50% three and 50% four.

*Sepal shape*.—Elliptical to narrowly lanceolate, moderately recurved.

*Sepal margin*.—Entire, very slightly ruffled.

*Sepal size*.—Width in the middle 2.3 cm and 10.3 cm long.

*Sepal aspect*.—Moderately recurved.

*Sepal surface*.—Glabrous, smooth surface.

*Sepal apex*.—Acute.

*Sepal base*.—Fused.

*Sepal color*.—Both surfaces R.H.S. 7A, Yellow base with RHS 154B, Yellow-Green to form slightly green throat.

*Pedicel size*.—Average 1.0 cm in length and 4mm in width.

*Pedicel shape*.—Ovoid, three sided.

*Pedicel color*.—R.H.S. 144A, Yellow-Green; and.

*Pedicel strength/aspect*.—Moderately strong, held at about 20° relative to peduncle.

*Peduncle color*.—R.H.S. 137C, green.

*Peduncle strength*.—Rigid and sturdy.

Reproductive organs:

(1) *Gynoecium* (*female*).—One pistil per flower. Pistil varies with some pistils corkscrewing around inside flower, some very short (3 cm) and an average length of 7.8 cm and 1 mm in width with color RHS12C, Yellow, some are longer with multiple branches near the apex, less than 40% have an average length of about 9 cm and a width on average 1 mm, approximately 90% of ovaries are 5 mm in length and an average width of 4 mm and color RHS 138B, Green; ovules base color RHS 11B, Yellow, apex (Stigma) RHS 12C, Yellow (note particularly FIG. 3).

Figure 3:
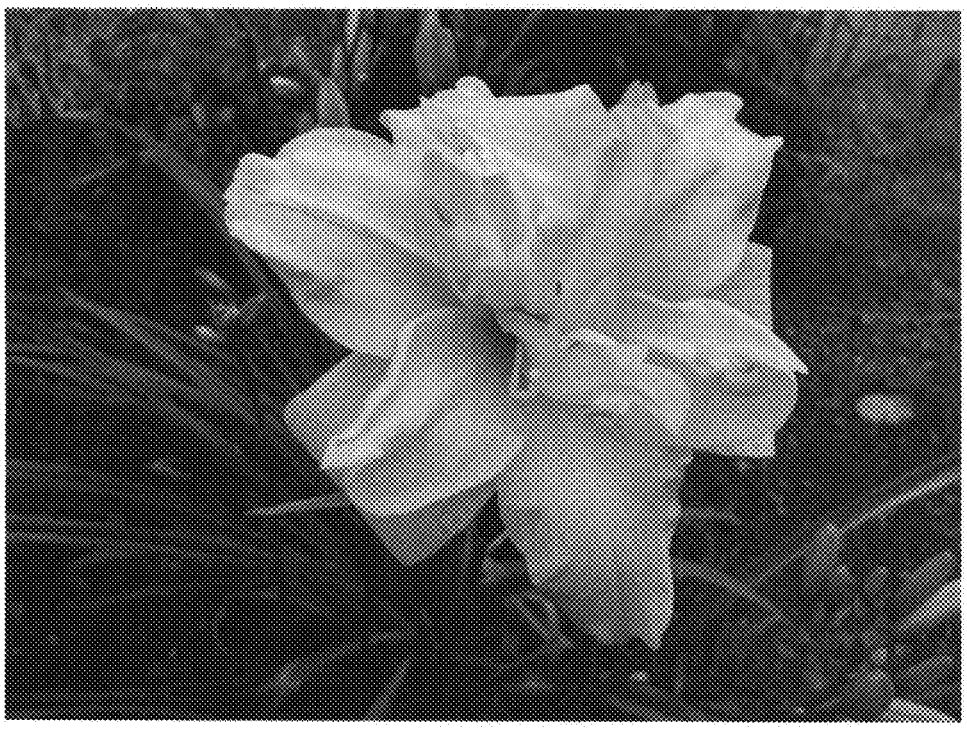
FIG. 3 shows some of the unique sexual structures of 'Connie Marks', including petaloids with anthers.

(2) *Androecium* (*male*).—Stamen (anther and filament) — the number of filament anthers and petaloid anthers varies with the greatest number observed being six petaloid anthers and three filament anthers, petaloid color RHS 7A, Yellow (note again FIG. 3). Pollen — color RHS 16A, Yellow-Orange, moderate in quantity for anthers. Stamens — Average filament length 6.8 cm, width 1 mm, filament color RHS 11 A, Yellow, anthers measure on average a total of 6.17 mm in length for anthers with color RHS 17A, Yellow-Orange.

Fragrance: Light perfume like fragrance similar to cultivar 'Hyperion'.

Habitat in Culpeper, Virginia experiences a normal summer; daytime high temperature ranges between 24°-34° C., with a nighttime low temperature range of 9° to 20° C.

Fruit/seeds: No fruit or seeds have been observed to date.

What is claimed is:

1. A new and distinct cultivar of *Hemerocallis* plant named 'Connie Marks' as illustrated and described herein.

* * * * *